United States Patent
Saari et al.

(10) Patent No.: US 7,404,334 B2
(45) Date of Patent: Jul. 29, 2008

(54) TESTING SYSTEM WITH SOFT REACTION STRUCTURE

(75) Inventors: Byron J. Saari, Minneapolis, MN (US); Craig L. Campbell, Maple Grove, MN (US)

(73) Assignee: MTS Systems Corporation, Eden Prairie, MN (US)

( * ) Notice: Subject to any disclaimer, the term of this patent is extended or adjusted under 35 U.S.C. 154(b) by 107 days.

(21) Appl. No.: 11/478,164

(22) Filed: Jun. 29, 2006

(65) Prior Publication Data

US 2008/0011094 A1   Jan. 17, 2008

(51) Int. Cl.
*G01B 5/30* (2006.01)

(52) U.S. Cl. .......................................... 73/856; 73/760

(58) Field of Classification Search .................. 73/49.4, 73/833, 781, 856, 816, 799, 150 A, 794, 760, 73/12.01, 787, 826
See application file for complete search history.

(56) References Cited

U.S. PATENT DOCUMENTS

| | | | | |
|---|---|---|---|---|
| 3,102,421 A | * | 9/1963 | Cosner et al. ................ | 374/49 |
| 3,142,980 A | * | 8/1964 | Andersen ..................... | 73/834 |
| 3,158,048 A | * | 11/1964 | Bollar ..................... | 72/453.06 |
| 3,297,284 A | * | 1/1967 | Pellerin ..................... | 248/550 |
| 3,442,120 A | | 5/1969 | Russenberger | |
| 3,589,278 A | * | 6/1971 | Brauer et al. ............... | 100/271 |
| 3,597,960 A | | 8/1971 | Otera | |
| 4,445,381 A | | 5/1984 | Russenberger | |
| 4,478,086 A | * | 10/1984 | Gram .......................... | 73/781 |
| 5,677,494 A | | 10/1997 | Keener | |
| 6,023,980 A | | 2/2000 | Owen | |
| 6,427,988 B1 | * | 8/2002 | Li .......................... | 267/140.11 |
| 6,601,456 B1 | * | 8/2003 | Davidson et al. .............. | 73/808 |
| 2004/0139804 A1 | * | 7/2004 | Takada et al. ................. | 73/760 |
| 2005/0050963 A1 | * | 3/2005 | Shelby ........................ | 73/809 |

FOREIGN PATENT DOCUMENTS

| | | |
|---|---|---|
| DE | 3102778 A1 | 12/1981 |
| GB | 1442 048 A | 7/1976 |
| JP | 57048632 A * | 3/1982 |
| WO | WO 98/37400 | 8/1998 |

OTHER PUBLICATIONS

Written Opinion of the International Searching Authority of the European Patent Office in couterpart foreign application No. PCT/US2007/015119 filed Jun. 28, 2007.*
Test Systems for Automobiles: Engine Test Systems, tp://www.saginomiya.co.jp/sikenki/carengin.html, copyright 2004, pp. 1-2.
Official Search Report of the European Patent Office in counterpart foreign application No. PCT/US2007/015119 filed Jun. 28, 2007.
Hoffelner W., Fatigue Crack Growth at 20 KHZ-A New Technique, Journal of Physics E. Scientific Instruments, IOP Publishing, Bristol, GB, vol. 13,No.6,Jun. 1980, pp. 617-619.

* cited by examiner

*Primary Examiner*—Edward Lefkowitz
*Assistant Examiner*—Jonathan Dunlap
(74) *Attorney, Agent, or Firm*—Steven M. Koehler; Westman, Champlin & Kelly, P.A.

(57) ABSTRACT

A testing system includes a soft reaction structure formed by column assemblies, a base and a crosshead. Compliant devices are disposed between the column assemblies and the base and/or the crosshead to isolate interaction of these components and reduce structural vibration mode excitation.

35 Claims, 4 Drawing Sheets

TESTING SYSTEM WITH SOFT REACTION STRUCTURE

BACKGROUND OF THE INVENTION

The discussion below is merely provided for general background information and is not intended to be used as an aid in determining the scope of the claimed subject matter.

The physical testing of materials and/or components by taking a test specimen and applying tension and/or compressive loads and/or displacements using an actuator is well known. Commonly, the tension and compression loads are applied to the test specimen in an alternating manner at a selected frequency, or through a range of frequencies at constant displacement or amplitude. In harmonic motion, such as present in this form of testing, the acceleration of moving components of the actuator, the specimen grips, etc. are proportional to the amount of displacement multiplied by the square of the frequency. Therefore, even if the amplitude is small (e.g. 0.06 mm), the acceleration can be very large at higher frequencies (e.g. 700-1000 Hertz).

Consequently, the force, which is proportional to the mass of the moving components times the acceleration, is also increasing by the square of the frequency, as the frequency increases. Moreover, this force must be reacted by the structure of the test system, which will cause excitation of modes in the test system.

A common test system construction includes a base with upstanding columns that support a crosshead over the base. A first specimen grip is coupled to the crosshead through the actuator, while a second specimen grip is coupled to the base through a force transducer; however the location of the actuator and force transducer can be reversed.

Due to the large dynamic forces, one mode of vibration is that the columns may stretch and compress allowing the crosshead to move up and down slightly. However, another mode of vibration that is also proving to be detrimental to testing is a box mode excited in the box-like construction of the crosshead, base and columns. These modes are detrimental because these modes causes the force transducer to move up and down, which induces an inertial error in its corresponding output signal. Many other vibration modes of this type can be conceptualized and these detrimental modes can be referred to as structural vibration modes.

SUMMARY OF INVENTION

This Summary and Abstract are provided to introduce some concepts in a simplified form that are further described below in the Detailed Description. This Summary and Abstract are not intended to identify key features or essential features of the claimed subject matter, nor are they intended to be used as an aid in determining the scope of the claimed subject matter. In addition, the description herein provided and the claimed subject matter should not be interpreted as being directed to addressing any of the short-comings discussed in the Background.

A testing system includes a soft reaction structure. The testing system includes a base and a pair of column assemblies extending upwardly from the base. A crosshead is joined to ends of the pair of column assemblies remote from the base. A pair of specimen holders is provided. A first specimen holder is supported by the base, while a second specimen holder is supported by the crosshead. Compliant devices are provided to form a compliant coupling between each of the column assemblies and at least one of the base and the crosshead. The compliant devices support the weight of the crosshead. Stated another way, the compliant devices reduce the transmitted vibrations from the crosshead and/or columns into the base.

DETAILED DESCRIPTION OF THE ILLUSTRATIVE EMBODIMENTS

Figure 1:
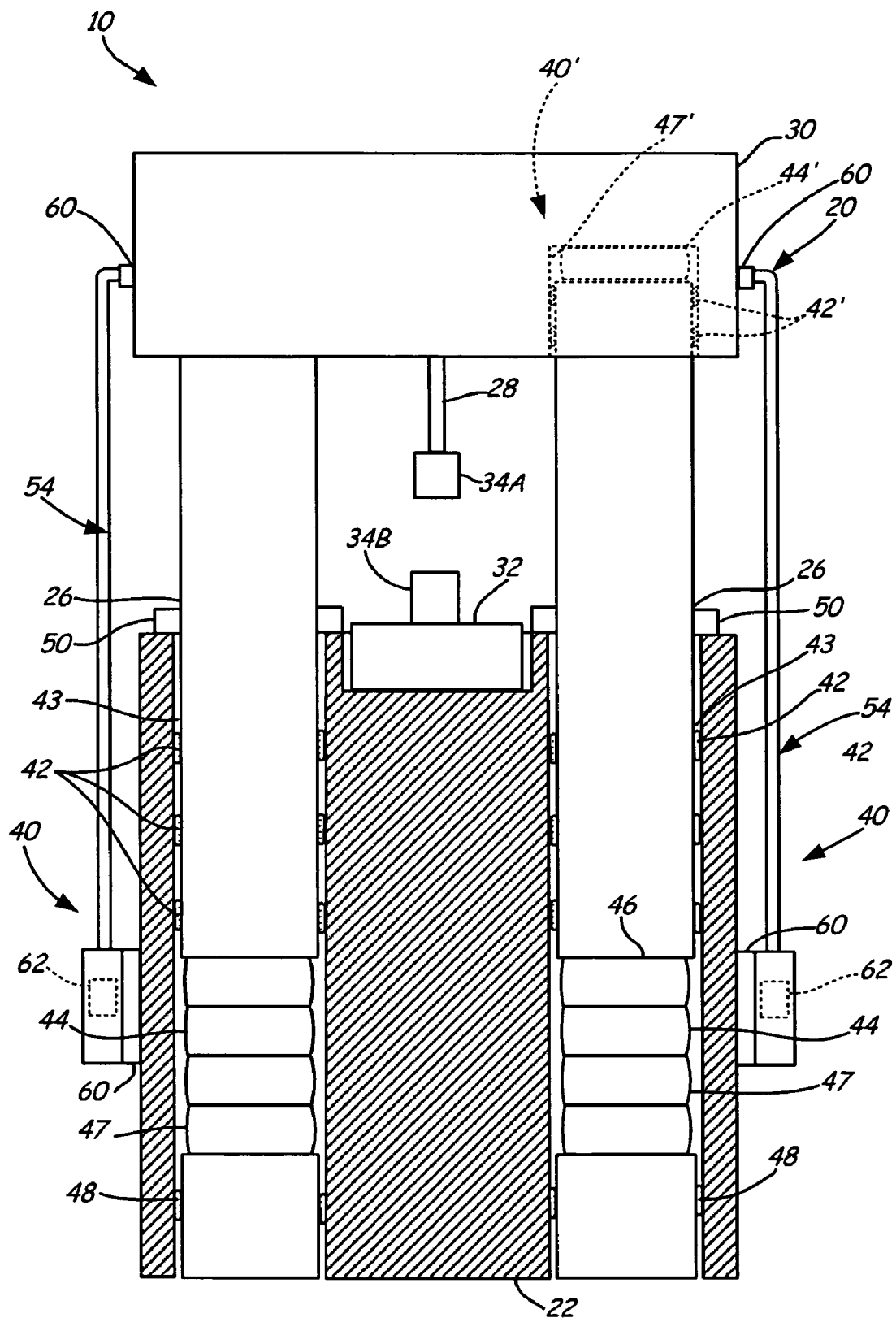
FIG. 1 is a schematic sectional view of a testing system.

A schematic sectional view of a testing system 10 for applying forces or motions to a test specimen is illustrated in FIG. 1. The testing system 10 includes a frame 20 having a base 22, a pair of column assemblies 26 that extend upwardly from the base 22, and a crosshead 30 coupling the ends of the column assemblies 26 remote from the base 22. In the embodiment illustrated, an actuator 28 is coupled to the crosshead 30, while a force transducer 32 is coupled to the base 22. An upper test specimen holder 34A and a lower test specimen 34B are coupled to the actuator 28 and the force transducer 32, respectively.

One concept herein described provides structural vibration mode isolation and/or damping in the testing system 10. In the embodiment illustrated, column assemblies 26 are isolated from base 22 using compliant devices that function as soft springs elements. In one embodiment, the compliant devices comprise gas filled inflatable elements or chambers 40 disposed between each column assembly 26 and the base 22, and wherein said elements are spaced apart from each other along the length of the column assembly 26. For instance, the inflatable elements 40 can include circular shaped tubes 42 having a center aperture 43 through which the corresponding column assembly 26 can extend. The tubes 42 can include zones or chambers about the perimeter thereof so that gas does not merely move from one side to the other during displacement of the column assemblies 26, but rather is contained to provide desired resistance.

The inflatable elements or chambers 40 can also include one or more inflatable cells or bellows 44 disposed between a lower end 46 of each column assembly 26 and ground and/or base 22, thereby supporting the weight of the crosshead 30 and components of the column assemblies 26 above the cells 44. However in a further embodiment, the inflatable cells or bellows 44 can be replaced with a sealed, pressurizable chamber 47 formed between the lowermost circular shaped tube 42 and an additional circular shaped tube 48.

Components of the construction described above substantially decouple or isolate (with respect to a rigid connection using rigid components) each column assembly 26 from base 22 in up to six degrees of freedom. In particular, the inflatable cells 44 or gas filled chambers provide primary vertical isolation, while tubes 42 provide linear isolation along axes perpendicular to the vertical axis as well as isolation for all moments about the axes and some secondary vertical isolation through their shear stiffness. At this point it should be noted that the tubes 42 need not be continuous about the perimeter of each column assembly 26, but rather can be a plurality of spaced apart elements, if desired. Furthermore, the elements could be individually adjustable, for example, by gas pressure, to provide desired compliance where needed (i.e. adjustable and/or variable compliance along or about one or more selected axes). In other words, the compliant devices herein described provide adjustability in the testing system 10. In particular, use of gas filled or pneumatic components and/or chambers allows the compliance between the column assemblies 26 and the base 22 to be adjustable. Nevertheless, the gas filled elements or chambers 40 are but one embodiment in that other compliant structures and/or materials can also be used.

The location of the compliant devices on the testing system 10 is advantageous in that it allows the testing system 10 to operate as a conventional testing system. In particular, column clamps 50 (schematically indicated) can be provided so as to selectively, rigidly couple each column assembly 26 to the base 22. When the column clamps 50 are used, the compliant devices can be deactivated (for example, gas pressure is released). With the column clamps 50 activated loads can be applied to the test specimen, for instance, sinusoidal loads can be applied at lower frequencies, for example. However, for higher load frequencies, including the resonant frequency of the testing system 10 with the compliant devices activated the column clamps 50 can be deactivated and the testing system 10 can then utilize the compliant devices to provide isolation and/or damping of the column assemblies 26 from the base 22.

Although described wherein the compliant devices are disposed between the column assemblies 26 and the base 22, in a further embodiment, the compliant devices can be disposed between the column assemblies 26 and the crosshead 30, in addition or in the alternative to that described above. This construction is illustrated in FIG. 1 by dashed elements or chambers 40', 42', 44' and 47', denoting elements or chambers similar to that of elements or chambers 40, 42, 44 and 47 respectively. In this embodiment, the element 44' or chamber 47' supports the weight of the crosshead 30.

As is known in the art, suitable lifts 54 (e.g. hydraulic, although other forms such as screw driven, pneumatic, electric, etc. can also be used) are often used to move the crosshead 30 to a selected position. In view that the lifts 54 can provide a load path between the crosshead 30 and the base 22, it may be also desirable to isolate this load path with a compliant device. The compliant device can take a number of forms. For example, a soft spring element such as an elastomeric coupling 60 can be provided at the crosshead 30 and/or the base 22. In the alternative, or in addition, a gas filled cell or chamber 62 can be used.

Figure 2:
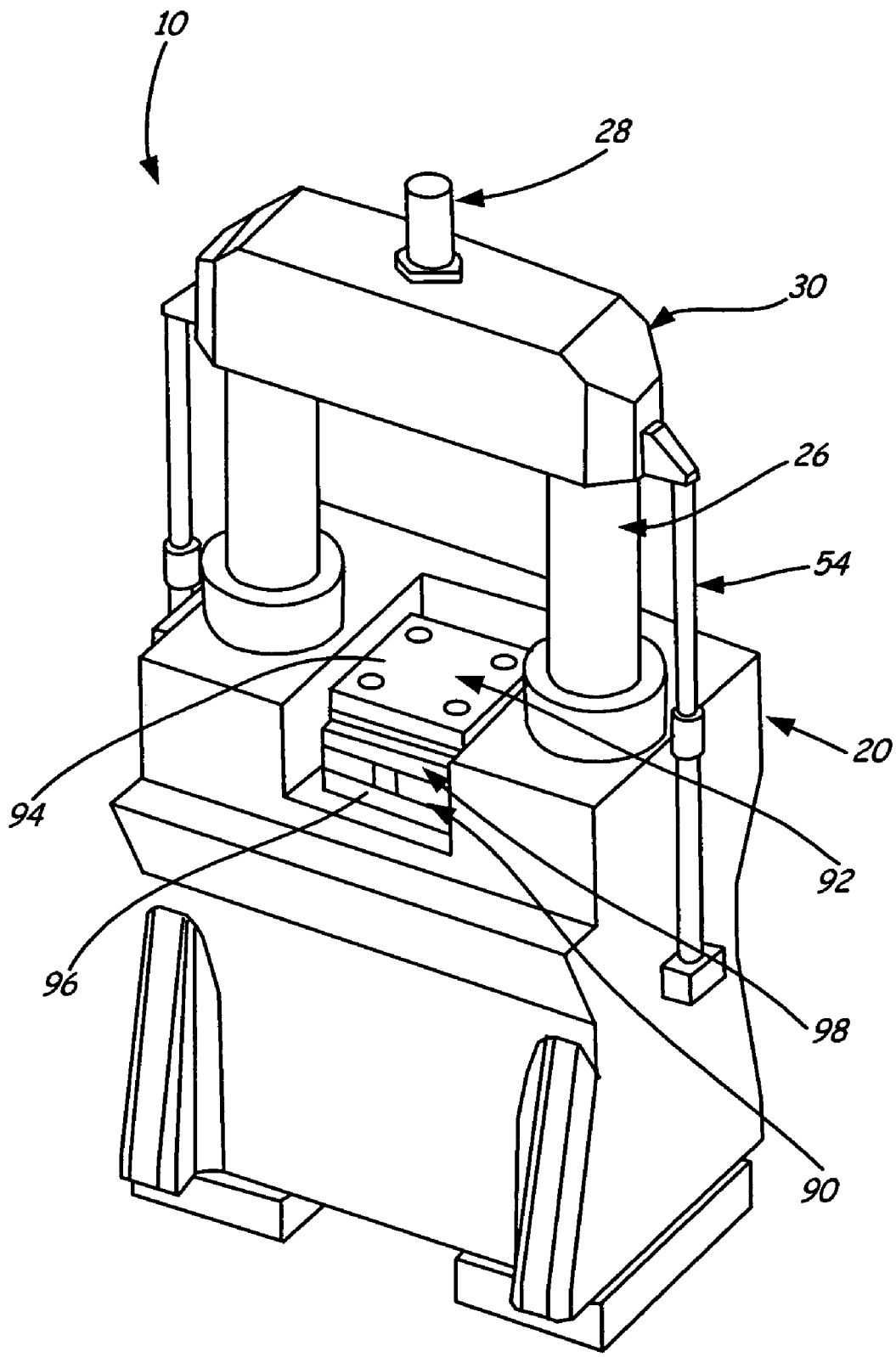
FIG. 2 is a perspective view of a testing system.
Figure 3:
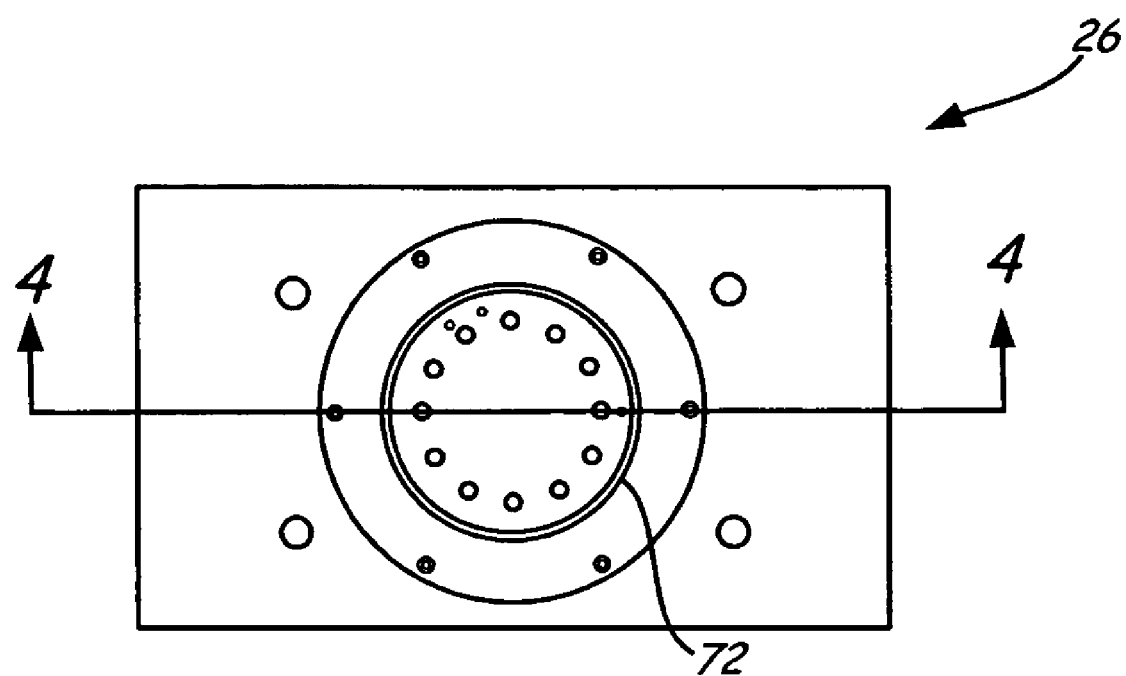
FIG. 3 is a top view of a column assembly of the testing system of FIG. 2.
Figure 4:
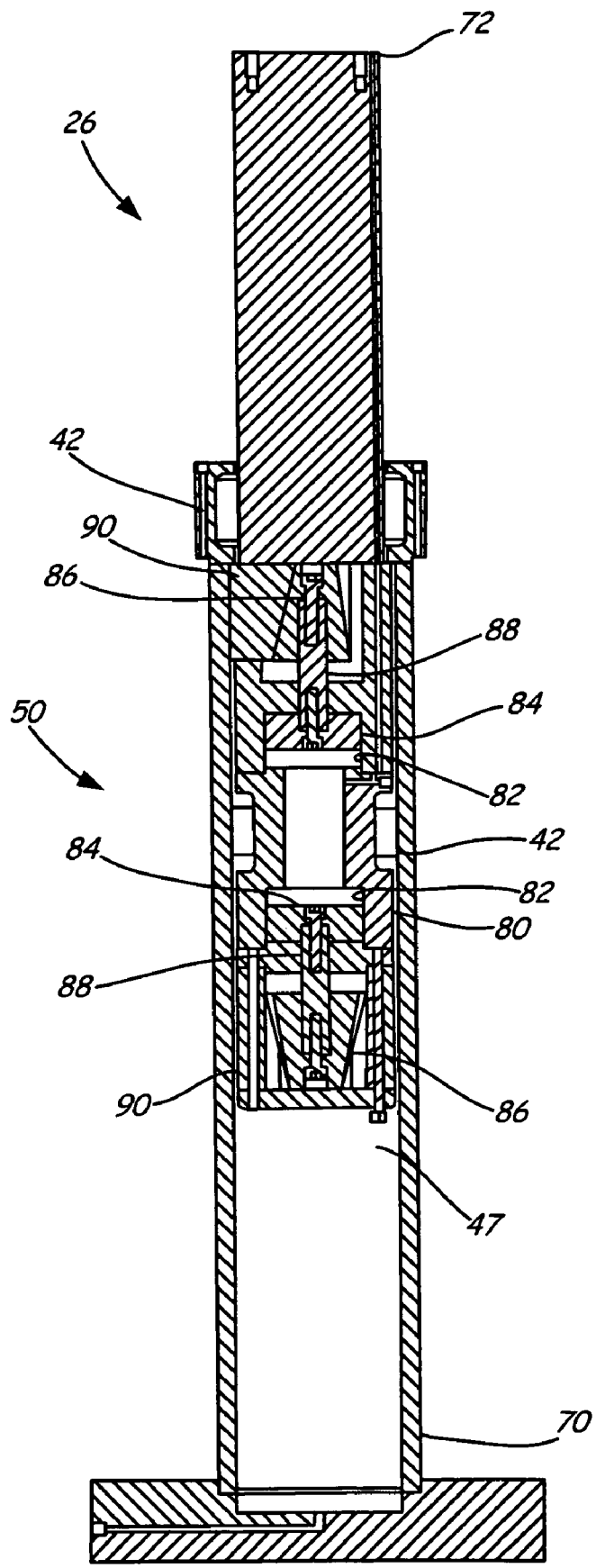
FIG. 4 is a sectional view of the column assembly taken along line 4-4 of FIG. 3.

FIG. 2 is a perspective view of an embodiment of the testing system 10, while FIGS. 3 and 4 illustrate an exemplary column assembly 26 in detail, where similar components have been identified with same reference numbers as described above. In this embodiment, the column assembly 26 includes a column sleeve 70 on a lower portion thereof and an upper solid column portion 72. Two tubes 42 are used with the gas filled chamber 47. One of the tubes 42 is disposed above the column clamp 50, while the other is disposed below the column clamp 50.

The column clamp 50 includes a center support cylinder assembly 80 with cylinders 82 configured to receive pistons 84 in order to provide to actuator assemblies. Each piston 84 is coupled to a cone shaped wedge 86 through a rod 88. The cone shape 86 is configured to operate with a receiver assembly 90 having wedge shaped elements disposed annularly about the wedge 86 such that movement of the wedge 86 as driven by the piston 84 will cause the wedge shaped elements of the receiver assembly 90 to engage the inner wall of the columns sleeve 70.

In the embodiment of FIG. 2, the testing system 10 includes a horizontal actuator assembly 90 in addition to the vertical actuator assembly 28. The horizontal actuator assembly 90 includes a load table 92 to which the force transducer (not shown) can be attached. The load table 92 includes an upper platen 94 and a lower platen 96 where the upper platen 94 and the lower platen 96 are coupled together with a linear bearing assembly 98 and an actuator (not shown). Although the horizontal actuator assembly 90 is not required in each testing system 10, if present, the compliant devices herein described can be beneficial for the reasons discussed above with respect to the vertical actuator 28. Likewise, if a rotary actuator is present in the testing system 10 to apply moment or twisting loads to a test specimen, the compliant devices can also be beneficial.

In summary, a soft reaction structure is provided for a testing system so as to isolate the column assemblies 26 from the base 22 and/or crosshead 30. Compliant devices disposed between the column assemblies 26 and the base 22 and/or crosshead 30 isolate interaction of these components and reduce transmitted structural mode vibrations thereby reducing the excited motion of the force transducer, thereby improving the range of performance and/or accuracy of results obtained.

Although the subject matter has been described in language specific to structural features and/or methodological acts, it is to be understood that the subject matter defined in the appended claims is not limited to the specific features or acts described above as has been held by the courts. Rather, the specific features and acts described above are disclosed as example forms of implementing the claims.

What is claimed is:

1. A material testing system comprising:
    a base;
    a pair of column assemblies, each column assembly having a column extending upwardly along a vertical axis, each column having a vertical outer surface about its vertical axis and along its length;
    a crosshead joined to ends of the pair of column assemblies remote from the base;
    a pair of specimen holders, wherein a first specimen holder is supported by the base and a second specimen holder is supported by the crosshead;
    a compliant coupling for each column configured to selectively engage and provide compliance between the vertical outer surface of the column and at least one of the base and the crosshead, said compliance being along an axis orthogonal to the vertical axis.

2. The testing system of claim 1 and further comprising a sealed, pressurizable chamber for each column assembly to support the weight of the crosshead.

3. The testing system of claim 1 wherein each compliant coupling comprises an inflatable cell.

4. The testing system of claim 1 wherein each compliant coupling is disposed between each column and the base.

5. The testing system of claim 1 wherein each compliant coupling comprises a first compliant element engaging the vertical surface and a second compliant element engaging the vertical surface, the second compliant element being spaced apart from the first compliant element along each respective column.

6. The testing system of claim 5 wherein the first compliant element and the second compliant element each comprise inflatable tubes.

7. The testing system of claim 6 and further comprising a sealed, pressurizable chamber disposed below each column to support the weight of the each column.

8. The testing system of claim 6 and further comprising an inflatable cell disposed below each column.

9. The testing system of claim 6 wherein each compliant element is disposed between each respective column and the crosshead.

10. The testing system of claim 6 wherein each compliant element is disposed between each respective column and the base.

11. A testing system comprising:
a base;
a pair of column assemblies extending upwardly;
a crosshead joined to ends of the pair of column assemblies remote from the base;
a pair of specimen holders, wherein a first specimen holder is supported by the base and a second specimen holder is supported by the crosshead;
a compliant coupling that is configured selectively to couple each of the column assemblies and at least one of the base and the crosshead with compliance so as to reduce box mode excitation of the base, pair of column assemblies and the crosshead.

12. The testing system of claim 11 wherein the compliant coupling comprises a sealed, pressurizable chamber for each column assembly.

13. The testing system of claim 11 wherein the compliant coupling comprises an inflatable cell.

14. The testing system of claim 11 wherein the compliant coupling comprises a compliant element having a center aperture through which a portion of the column assembly extends.

15. The testing system of claim 14 wherein the compliant coupling comprises a second compliant element spaced apart from the first-mentioned compliant element along the column assembly, wherein the second compliant element includes a center aperture through which a portion of the column assembly extends.

16. The testing system of claim 15 wherein the first-mentioned compliant element and the second compliant element comprise inflatable tubes.

17. The testing system of claim 16 and further comprising a sealed, pressurizable chamber disposed below each column assembly.

18. The testing system of claim 16 and further comprising an inflatable cell disposed below each column assembly.

19. The testing system of claim 18 wherein the compliant coupling is disposed between the column assemblies and the crosshead.

20. The testing system of claim 18 wherein the compliant coupling is disposed between the column assemblies and the base.

21. A testing system comprising:
a base;
a pair of column assemblies extending upwardly;
a crosshead joined to ends of the pair of column assemblies remote from the base;
a pair of specimen holders, wherein a first specimen holder is supported by the base and a second specimen holder is supported by the crosshead;
a mechanism configured to selectively rigidly join each column assembly to the base or the crosshead;
a first compliant coupling disposed between each of the column assemblies and at least one of the base and the crosshead and configured to provide compliance along an axis orthogonal to a vertical axis of each column assembly when the mechanism is not rigidly joining each column assembly to the base or the crosshead; and
a second compliant coupling configured to support at least the weight of the crosshead.

22. The testing system of claim 21, wherein the first compliant coupling comprises a sealed, pressurizable chamber for each column assembly.

23. The testing system of claim 21, wherein the first compliant coupling comprises an inflatable cell.

24. The testing system of claim 21 wherein said first compliant coupling comprises a compliant element disposed between each column assembly and the base, wherein the compliant element includes a center aperture through which a portion of the column assembly extends.

25. The testing system of claim 24 wherein said first compliant coupling comprises a second compliant element disposed between each column assembly and the base and spaced apart from the first-mentioned compliant element along the column assembly, wherein the second compliant element includes a center aperture through which a portion of the column assembly extends.

26. The testing system of claim 25 wherein the first-mentioned compliant element and the second compliant element comprise inflatable tubes.

27. The testing system of claim 26, wherein the second compliant coupling comprises a sealed, pressurizable chamber disposed below each column assembly.

28. The material testing system of claim 26, wherein the first compliant coupling comprises an inflatable cell disposed below each column assembly.

29. The testing system of claim 21, wherein the second compliant coupling comprises an inflatable cell disposed between each column assembly and the crosshead.

30. The testing system of claim 21 wherein each compliant coupling is configured to engage the corresponding vertical outer surface of the column with compliance so as to reduce box mode excitation of the base, pair of column assemblies and the crosshead.

31. The testing system of claim 11 wherein each compliant coupling is configured to selectively engage the corresponding vertical outer surface of the column to provide said compliance.

32. The testing system of claim 11 and further comprising clamps to selectively rigidly clamp a column of each column assembly to the base or crosshead.

33. The testing system of claim 1 wherein each of the compliant couplings is configured to engage the corresponding column assembly with compliance so as to reduce box mode excitation of the base, pair of column assemblies and the crosshead.

34. The testing system of claim 1 wherein each of the compliant couplings is adjustable to provide adjustable compliance along and/or about an axis that is orthogonal to the vertical axis.

35. The testing system of claim 34 wherein each of the compliant couplings comprise a plurality of selectively inflatable chambers disposed about each respective vertical axis.

* * * * *